United States Patent
Mauran et al.

(10) Patent No.: US 10,577,140 B2
(45) Date of Patent: *Mar. 3, 2020

(54) METHOD AND DEVICE FOR STERILE PACKAGING OF A READY-TO-USE FLEXIBLE HYDROPHILIC INTRAOCULAR LENS

(71) Applicant: ALTACOR LIMITED, Cambridge (GB)

(72) Inventors: Christian Mauran, Saint Jean (FR); Mathieu Guillaume, Annecy le Vieux (FR)

(73) Assignee: ALTACOR LIMITED, Cambridge (GB)

( * ) Notice: Subject to any disclaimer, the term of this patent is extended or adjusted under 35 U.S.C. 154(b) by 89 days.

This patent is subject to a terminal disclaimer.

(21) Appl. No.: 15/670,910

(22) Filed: Aug. 7, 2017

(65) Prior Publication Data

US 2017/0334588 A1  Nov. 23, 2017

Related U.S. Application Data

(63) Continuation of application No. 10/580,914, filed as application No. PCT/FR03/03575 on Dec. 3, 2003, now Pat. No. 9,751,649.

(30) Foreign Application Priority Data

Dec. 4, 2002 (FR) .................................... 02 15294

(51) Int. Cl.
*B65B 25/00* (2006.01)
*A61F 2/16* (2006.01)
(Continued)

(52) U.S. Cl.
CPC ............ *B65B 25/008* (2013.01); *A61F 2/167* (2013.01); *A61F 2/1664* (2013.01);
(Continued)

(58) Field of Classification Search
CPC ........ A61F 2/67; A61F 2/1691; A61F 2/1662; A61F 2/1664; A61F 2/1667; A61F 2/167;
(Continued)

(56) References Cited

U.S. PATENT DOCUMENTS 3,930,580 A   1/1976 Bazell et al.
3,938,638 A   2/1976 Moule
(Continued)

FOREIGN PATENT DOCUMENTS

CN   1602173 A   3/2005
WO   WO 96/15743 A1   5/1996
(Continued)

OTHER PUBLICATIONS

European Patent Office Communication mailed in the correspond EP Appliation No. 09 779 175.0 dated Oct. 1, 2013 (6 pages).

*Primary Examiner* — Diane D Yabut
(74) *Attorney, Agent, or Firm* — Birch, Stewart, Kolasch & Birch, LLP (57) ABSTRACT

The invention relates to a method and a device for packaging a flexible hydrophilic intraocular lens (1) placed flat on an injection support (4) which is adapted to carry out folding of the lens (1) during its implantation. The lens is immersed in a bath of liquid conserving solution contained in a sealed flask (30) which is itself enclosed in a packaging envelope (48), the assembly being steam-sterilized.

13 Claims, 5 Drawing Sheets

(51) Int. Cl.
*A61M 5/315* (2006.01)
*B65B 55/02* (2006.01)

(52) U.S. Cl.
CPC .......... *A61F 2/1691* (2013.01); *A61M 5/315* (2013.01); *A61M 5/31501* (2013.01); *B65B 55/02* (2013.01)

(58) Field of Classification Search
CPC .... A61F 2/1672; A61F 2/1675; A61F 2/1678; A61M 5/315; A61M 5/31501; A61M 5/31511; A61M 5/31513; B65B 25/008
See application file for complete search history.

(56) References Cited

U.S. PATENT DOCUMENTS

| | | |
|---|---|---|
| 4,423,809 A | 1/1984 | Mazzocco |
| 4,573,998 A | 3/1986 | Mazzocco |
| 4,787,904 A | 11/1988 | Severin et al. |
| 4,860,885 A | 8/1989 | Kaufman et al. |
| 5,425,734 A | 6/1995 | Blake |
| 5,616,148 A | 4/1997 | Eagles et al. |
| 5,728,102 A | 3/1998 | Feingold et al. |
| 5,860,984 A | 1/1999 | Chambers et al. |
| 5,873,879 A | 2/1999 | Figueroa et al. |
| 6,048,348 A | 4/2000 | Chambers et al. |
| 6,129,733 A | 10/2000 | Brady et al. |
| 6,334,862 B1 | 1/2002 | Vidal et al. |
| 6,387,101 B1 | 5/2002 | Butts et al. |
| 6,413,236 B1 | 7/2002 | Van Dyke |
| 6,425,885 B1 | 7/2002 | Fischer et al. |
| 2002/0156486 A1 | 10/2002 | Nadel |
| 2004/0199174 A1 | 10/2004 | Herberger et al. |
| 2005/0125000 A1 | 6/2005 | Tourrette et al. |
| 2005/0240159 A1 | 10/2005 | Kito et al. |
| 2010/0106160 A1 | 4/2010 | Tsai |

FOREIGN PATENT DOCUMENTS

| | | |
|---|---|---|
| WO | WO 96/28121 A1 | 9/1996 |
| WO | WO 98/20819 A1 | 5/1998 |
| WO | WO 2010/048096 A1 | 4/2010 |

METHOD AND DEVICE FOR STERILE PACKAGING OF A READY-TO-USE FLEXIBLE HYDROPHILIC INTRAOCULAR LENS

CROSS-REFERENCE TO RELATED APPLICATIONS

This application is a Continuation of U.S. patent application Ser. No. 10/580,914 filed on May 30, 2006, now U.S. Pat. No. 9,751,649, which was filed as the National Phase of PCT International Application No. PCT/FR2003/003575 filed on Dec. 3, 2003, which claims the benefit of priority to French Application No. 02/15294 filed on Dec. 4, 2002, all of which are hereby expressly incorporated by reference into the present application.

BACKGROUND OF THE INVENTION

The invention relates to a method and a device for packaging and conserving in a sterile condition a flexible hydrophilic intraocular lens which is ready to use, i.e. ready to be implanted by injection through an incision formed in the wall of a patient's eye.

Flexible intraocular lenses have the advantage of being able to be folded, allowing them to pass through incisions of small dimensions. To achieve this folding and injection of the lens into the eye, various devices have been proposed. For example, WO 9628121 and WO 9615743 propose, in the case of lenses which can be conserved dry (made of non-hydrophilic materials such as silicones), disposable injection devices comprising a folding cartridge and an injection device. The lens can be loaded into the cartridge before packaging and steam sterilization in an autoclave.

WO 9820819 also describes a packaging device for an injection kit for a non-hydrophilic lens, comprising a chamber for storing the lens in the non-folded state, and a device for transferring and folding the lens in an injector chamber. The assembly is held on a support plate itself enclosed by an envelope. In this case, too, the assembly can be sterilized.

However, such devices are not compatible with intraocular lenses called hydrophilic lenses, made of hydrophilic material(s) which need to be kept in a hydrated state for conservation.

Throughout the present text the term "hydrophilic lens" refers to any lens formed by a material such that it needs to be maintained in a liquid solution for conservation before use. Such lenses may be made, for example, of materials referred to as "hydrogel", "acrygel" or "acrylic" (the latter term deviating from its normal meaning), which materials are PMMA (polymethylmethacrylate) and/or HEMA (hydroxymethylmethacrylate), hydrated to more than 16%, in particular between 24% and 28%. U.S. Pat. No. 4,787,904 also describes various examples of materials that may be used to produce a hydrophilic lens.

Hydrophilic lenses have the particular advantage of good biocompatibility. In particular, they are compatible with natural aqueous humor from the chemical, physical and optical (appropriate angle of contact) points of view. In addition they have high flexibility, allowing them to be folded and/or rolled to facilitate their insertion through an incision of reduced dimensions, in particular through the incision formed to introduce into the eye the material necessary for the prior surgical treatment (for example, an incision of 3 mm to 3.5 mm for ablation of the lens by phaco-emulsification). In addition they have at the same time good shape memory, so that they regain their initial functional shape after insertion into the eye.

However, the problem arising with these hydrophilic lenses is precisely that of folding and manipulating them at the moment of the surgical act. U.S. Pat. No. 4,787,904 proposes to conserve the lens in the pre-folded state in the injection device while being immersed in a conserving solution, the whole assembly being contained in a flexible packaging pocket. However, this method cannot be used in practice, for two main reasons. Firstly, a lens which has remained folded for a long period before use necessarily retains a shape memory of the folded state and therefore does not regain its perfect initial functional shape after implantation.

In addition, such packaging cannot be steam-sterilized (autoclave) after production. The liquid solution in the pocket would cause excess pressure, leading to explosion of the pocket. The production of such a package is therefore not compatible with the imperative requirements of sterilizing the lens and its packaging.

As a result, hydrophilic lenses up to now have been conserved flat in sterilized rigid flasks of conserving solution. At the moment of the surgical act, the surgeon removes the lens using a pincer, folds it (optionally with the aid of a folding device) or places it in a folding/injection cartridge or in an injector and injects it into the eye. All these manipulations are relatively complex and delicate, increasing the risk of contamination and damage to the lens.

SUMMARY OF THE INVENTION

It is therefore an object of the invention to mitigate these disadvantages by proposing a method and a device for packaging a flexible hydrophilic intraocular lens by which:
  the lens is conserved flat in a liquid conserving solution and is folded only at the moment of the surgical act;
  sterility of the packaging and of the lens is easily achieved and can be guaranteed up to implantation, despite the presence of the liquid conserving solution;
  the packaging is sealed and does not present any risk of leakage of the liquid conserving solution before, during or after sterilization;
  the lens does not have to be manipulated at the time of implantation, either to fold it or to inject it.

Furthermore, it is an object of the invention to propose a method and a device for packaging which are simple and inexpensive. In particular, it is an object of the invention to propose a single-use packaging device which is disposable after implantation of the lens and is compatible with different models of lenses.

To achieve these objects, the invention relates to a method for packaging a flexible hydrophilic intraocular lens in which:
  the lens is placed on an injection support including an implantation end through which the lens can be slid and ejected for intraocular implantation, this injection support being adapted to receive and carry the lens and to be associated with an injection device including a thruster piston able to push the lens on the injection support towards the implantation end;
  the lens and the injection support are placed in a packaging containing a volume of liquid lens conserving solution which bathes the lens and keeps it hydrated, wherein:
  an injection support is used which is adapted to receive and carry the lens flat and to carry out folding of the lens before the latter is ejected via the implantation end;

the lens is placed flat on the injection support and is immersed in a bath of liquid conserving solution contained in a rigid liquid-tight flask which is closed;

the assembly is then steam-sterilized, in particular by being placed in an autoclave in a steam bath at high temperature (above 130° C., in particular 132° C., for more than 20 min, in particular 21 min).

According to the invention, before sterilization the rigid flask (containing the lens and the solution, and closed) is advantageously placed in an outer packaging envelope compatible with steam-sterilization.

The invention also includes a device for carrying out a method according to the invention.

The invention therefore also relates to a device for packaging and conserving in a sterile condition an intraocular lens, comprising:

an injection support including an implantation end through which the lens can be slid and ejected for intraocular implantation, said injection support being adapted to receive and carry the lens and to be associated with an injection device including a thruster piston able to push the lens on the injection support towards the implantation end;

a flexible hydrophilic intraocular lens placed on the injection support;

a packaging enclosing at least the lens, the injection support and a volume of liquid lens conserving solution which bathes the lens and keeps it hydrated, wherein:

said injection support is adapted to receive and carry the lens flat and to carry out folding of the lens before the latter is ejected via the implantation end;

the lens is carried flat on the injection support and is immersed in a bath of liquid conserving solution contained in a closed liquid-tight rigid flask, and the assembly is in the sterilized state.

According to the invention, the rigid flask is advantageously enclosed in an outer packaging envelope compatible with steam sterilization and the assembly is in the sterilized state.

The sterilized state of the device can be verified and guaranteed in a manner known per se, for example, by means of colored markings guaranteeing sterilization which are modified if the envelope is contaminated or risks being contaminated. The packaging device according to the invention includes at least the lens, the injection support and the liquid conserving solution in the rigid flask. It may contain other accessory elements.

According to the invention, use is advantageously made of an injection support adapted to carry out folding by a simple translational movement imparted to the lens when the latter is pushed towards the implantation end. Thus, the injection and folding support is without moving parts (only the piston being movable), which simplifies the packaging device and makes it more reliable. Folding (this term also including rolling) is achieved by means of guide surfaces, in particular helicoidal or tapering surfaces, formed in the injection support to guide the edge portions of the lens.

In a first variant of the invention use is made of an injection support carried detachably by a closing stopper of the rigid flask. The injection support, like the lens carried on it, is maintained immersed in the liquid solution in the flask by means of the stopper. At the time of use, the stopper is separated from the flask, then the injection support is separated from the stopper, then the injection support is associated with an injection device having a thruster piston. It should be noted that while this is done the lens is never manipulated, pinched or folded by tools; all risk of deterioration or contamination is therefore avoided.

In a second preferred embodiment of the invention, use is made of an injection support associated with an injection device including a hollow cylindrical body for receiving the thruster piston, which is adapted to slide in a sealed manner in the cylindrical body. In addition, the rigid flask and the cylindrical body are adapted to be fixed together rigidly in a sealed manner, the injection support extending into the liquid conserving solution in the rigid flask, but to be fixed together in such a way that they can be separated from one another in order to use the injection device for implantating the lens.

In this way the totality of the device necessary for implanting the lens by injection, including the lens, the injection and folding support and the injection device with thruster piston, are incorporated in the same packaging and are steam-sterilized together with the liquid solution and the rigid flask. At the time of use, it is sufficient to extract the injection device (carrying the injection support and the lens) from the packaging, to separate said injection device from the rigid flask and to inject the lens, without any additional handling. The term "hollow cylindrical body" refers to a body the internal wall of which has a generally cylindrical shape in the mathematical sense of the term, that is, having a cross-section which is not necessarily circular (although this shape, corresponding to a cylinder of revolution, is preferred), and which may be, for example, elliptical or other. The hollow cylindrical body and the thruster piston have conjugate shapes to ensure liquid-tightness between them, including during translational movements of the thruster piston in the hollow cylindrical body. They therefore form a device comparable to a syringe.

According to the invention, the rigid flask and the cylindrical body are advantageously fixed to one another by screwing one end of the rigid flask onto the outer wall of the cylindrical body. According to the invention, a seal is advantageously provided to ensure liquid-tightness between the rigid flask and the outer wall of the cylindrical body.

According to the invention, the device advantageously includes means forming an axial stop preventing premature extraction of the thruster piston from the hollow cylindrical body.

In this way extraction of the piston from the cylindrical body of the injection device during sterilisation or at the end of sterilisation, under the effect of the high pressure prevailing in the flask and in the injection support as a result of the sterilisation, is entirely avoided.

According to the invention, the hollow cylindrical body is advantageously adapted to form the axial end stop preventing premature extraction of the thruster piston from the hollow cylindrical body.

According to the invention, the device advantageously includes a seal adapted to be interposed between the axial end stop of the hollow cylindrical body and a sealing block of the thruster piston in its retracted end position in the hollow cylindrical body. This seal compressed between the sealing block and the axial stop ensures complete liquid-tightness, in particular during sterilization. As a variant, the axial stop may be formed by a rigid wall of the packaging envelope forming a receptacle for the injection device.

In addition, according to the invention the device is advantageously provided with unlockable means for locking the thruster piston in the retracted end position in the hollow cylindrical body. In this way any premature actuation of the thruster piston, which would risk damaging the lens, before utilization of the inventive device, is avoided. To achieve this, it is advantageously provided in a device according to the invention that the thruster piston includes an operating stem which is not rotationally symmetrical, that the hollow cylindrical body has an axial end provided with a non-rotationally-symmetrical opening having a shape matching that of the operating stem, and that the operating stem is mounted so as to be rotatable about its longitudinal axis between a locked position in which it cannot pass through the opening and an unlocked position in which it can pass through the opening.

In addition, according to the invention the injection support advantageously includes an adapter bush forming a receptacle for the lens, said bush being adapted to carry and receive different models of lenses, and said adapter bush also being adapted to be mounted in a cylindrical end portion of the injection support. In this way, the device according to the invention can be used with different types of lens without modification. Manufacturing costs are thus reduced.

The invention also includes a packaging method and device wherein there are in combination all or some of the characteristics mentioned hereinbefore or hereinafter.

BRIEF DESCRIPTION OF THE DRAWINGS

Other objectives, characteristics and advantages of the invention will be apparent from the following description with reference to the appended drawings representing embodiments of the invention which are given solely as non-limiting examples, in which drawings.

DETAILED DESCRIPTION OF THE INVENTION

A packaging device according to the invention is designed for packaging and conserving in a sterile condition a flexible hydrophilic intraocular lens 1 ready for use. Such a lens 1 comprises an optical portion 2 and two haptics 3. The lens 1 is placed on an injection support 4 including an implantation end 5 of tapered external shape, so as to be able to be introduced through an incision formed in the wall of a patient's eye. The dimensions and the interior shape of the implantation end are adapted to allow the lens 1 to pass through the implantation end and to be ejected from the implantation end 5 into the internal cavity of the eye.

In practice, the cross-section of the implantation end 5 may be circular, square or rectangular, or more generally polygonal, in particular as a function of the shape of the lens 1 in its folded state at the moment of ejection.

Opposite the implantation end 5 the injection support 4 includes a receptacle 6 for a lens 1 in the non-folded state (flat). The receptacle 6 is formed inside a substantially cylindrical end portion 7 of the injection support 4 and opens axially to form an aperture 8 through which the lens 1 can be inserted into the interior of the receptacle 6.

Between the receptacle 6 and the implantation end 5 the injection support 4 includes a folding cone 9 comprising an internal axial conduit 10 which communicates at one end with the receptacle 6 and at the other with the implantation end 5 and incorporates guiding/folding surfaces 11 adapted to guide the edge portions of the lens 1, in particular its optical portion 2, in such a way that the lens 1 is folded (or rolled) when it is displaced axially in translation inside the conduit 10 from the receptacle 6 to the implantation end 5. The external shape of the folding cone 9 is preferably substantially tapered so as to connect the outer wall of the cylindrical end portion 7 continuously to that of the implantation end 5. It should be noted, however, that as a variant any other form of truncated cone might be envisaged, in particular a truncated pyramid, or even a cylindrical shape.

The guiding/folding surfaces 11 of the conduit 10 of the folding cone 9 are formed by the opposed internal lateral walls of the conduit, which slope towards one another from the receptacle 6 to the implantation end 5.

The cylindrical end portion 7 of the injection support 4 is preferably provided with radial through-apertures 12 allowing the receptacle 6 to be supplied with liquid conserving solution from outside the injection support 4.

The outer wall 13 of the cylindrical end portion 7 of the injection support 4 includes fixing lugs 15 projecting radially to the exterior. The injection device 14 has a hollow cylindrical end 33 provided with apertures 16 adapted to receive the lugs 15 of the injection support so as to form quick-fastening means by non-return elastic engagement of the injection support 4 on the end of the injection device 14. The lugs 15 are in the form of latching elements and are adapted to deform elastically radially inwardly to engage in the apertures 16 when the injection support 4 is introduced axially into the end 33 of the injection device 14.

In the two first variants, shown in FIGS. 1 to 4, the injection support 4 is formed in a single piece constituting at the same time the receptacle 6, the guiding/folding surfaces 11 and the implantation end 5. However, in these variants it is necessary to design the precise shape of the receptacle 6 as a function of each model of lens 1 which is to be carried in said receptacle 6. In practice, flexible hydrophilic lenses 1 may have different shapes which vary from one another essentially by the shape and dimensions of their haptics. The lenses 1 also vary significantly in their dimensions.

Figure 5:
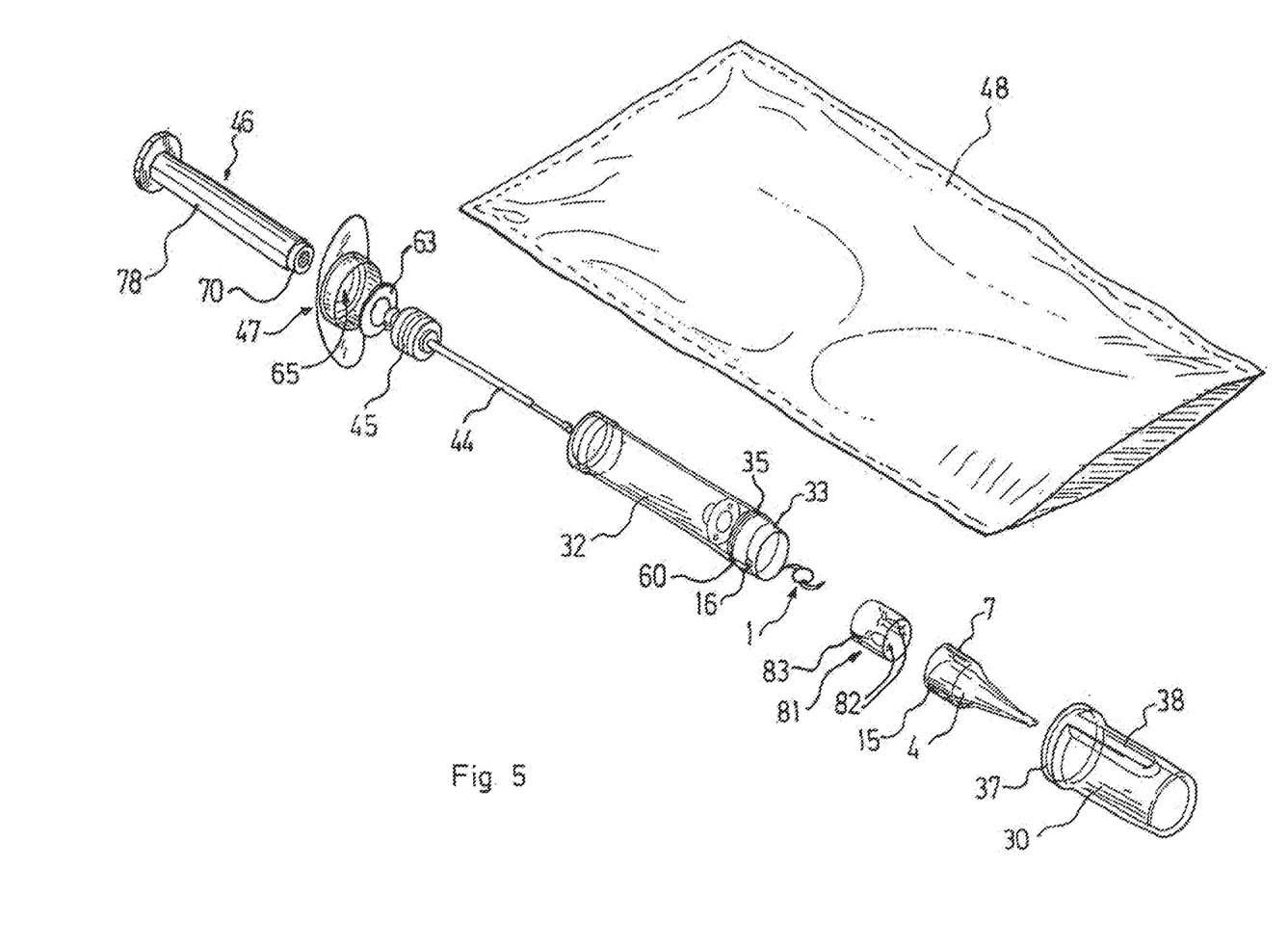
FIG. 5 is an exploded schematic perspective view showing a packaging device according to a third embodiment of the invention similar to the second embodiment, but with an injection support including an adapter bush.
Figure 6:
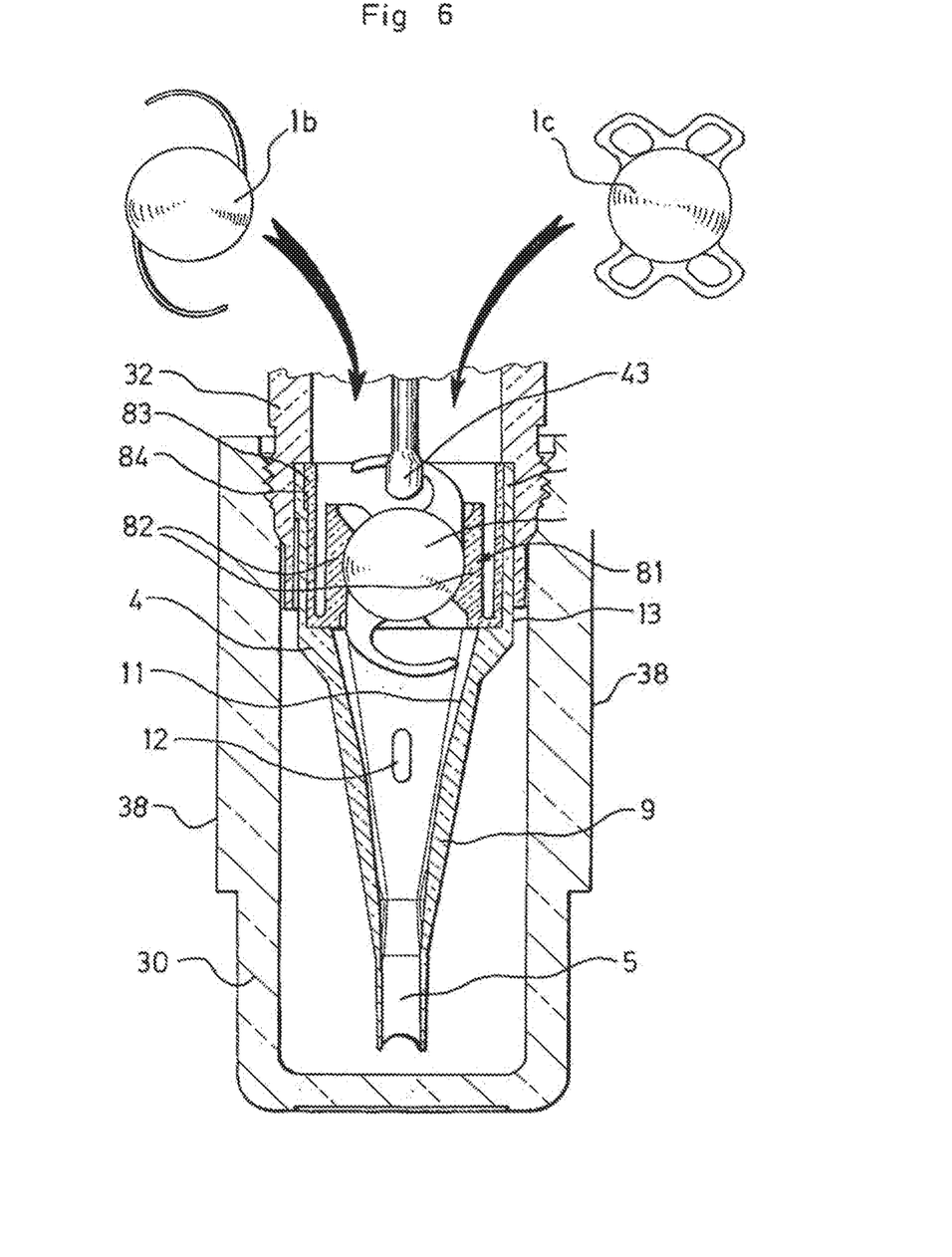
FIG. 6 is a schematic axial section showing a detail (end of injection device, injection support with bush and lens, and rigid flask) of the third embodiment of the invention.

To avoid having to produce the injection support 4 to match each model of lens 1 to be implanted, the third variant, shown in FIGS. 5 in 6, provides that the injection support 4 incorporates an adapter bush 81 designed to form the receptacle 6 for a lens 1, 1a, 1b, 1c of any model. Thus, said adapter bush 81 is able to carry and receive different lens models 1, 1a, 1b, 1c. The bush 81 is also adapted to be press-fitted into the cylindrical end portion 7 of the injection support 4.

The adapter bush 81 may be formed by a cylindrical sleeve open at both axial ends and having in its interior two lateral clips 82 extending axially opposite one another to receive the optical part of a lens 1, 1a, 1b, 1c. The clips 82 have shapes adapted to receive and retain the optical part of the lens 1, 1a, 1b, 1c while subsequently allowing its axial translation for the purpose of injection and while being compatible with different shapes of existing haptics. In FIG. 6, lens 1a has thick curved haptics, lens 1b has fine curved haptics and lens 1c is of the "navette" type having four haptics forming loops. These are non-limiting examples and other shapes of the lens 1 can be envisaged.

In practice, it will be noted that the adapter bush 81 shown in FIG. 6 can receive and carry these different models of lens 1. However, a plurality of models of the bush 81 to receive different types of lens 1 might equally be provided, at low manufacturing cost.

The cylindrical bush 81 can be introduced and press-fitted into the end portion 7 of the support 4. The bush 81 advantageously has an external rib 83 extending parallel to the axis of the bush 81 and adapted to engage in a matching groove 84 in the end portion 7 of the injection support 4, so as to mark and determine the angular position of the bush 81 with respect to the injection support 4.

The injection support 4 may be formed in one piece in rigid synthetic material, transparent or otherwise, adapted to withstand steam sterilization and made, for example, of polycarbonate or polymethacrylate.

Figure 1:
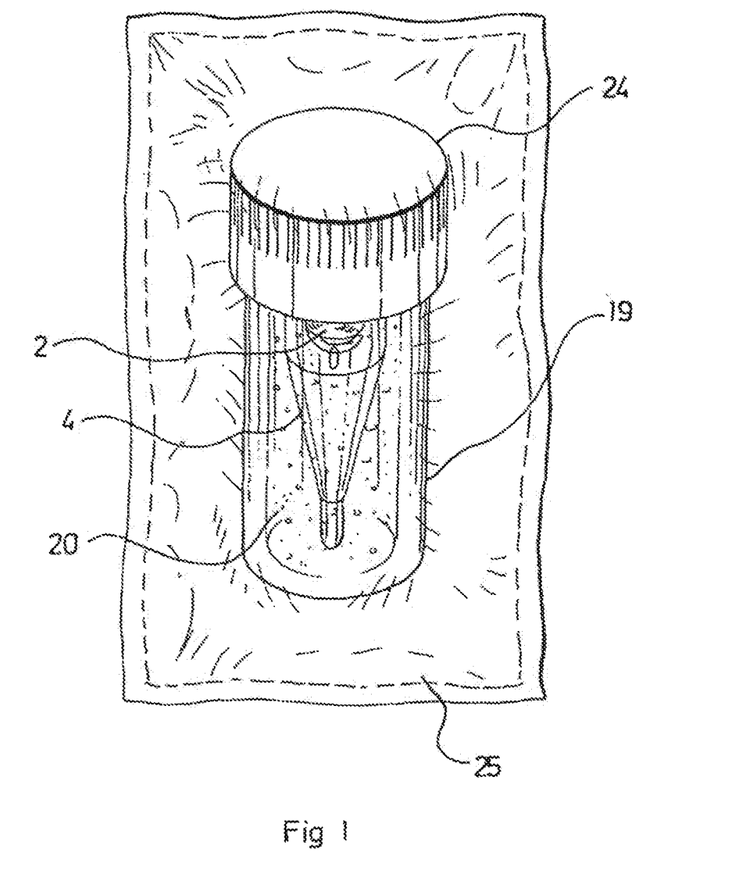
FIG. 1 is a schematic perspective view of a packaging device according to a first embodiment of the invention.
Figure 2:
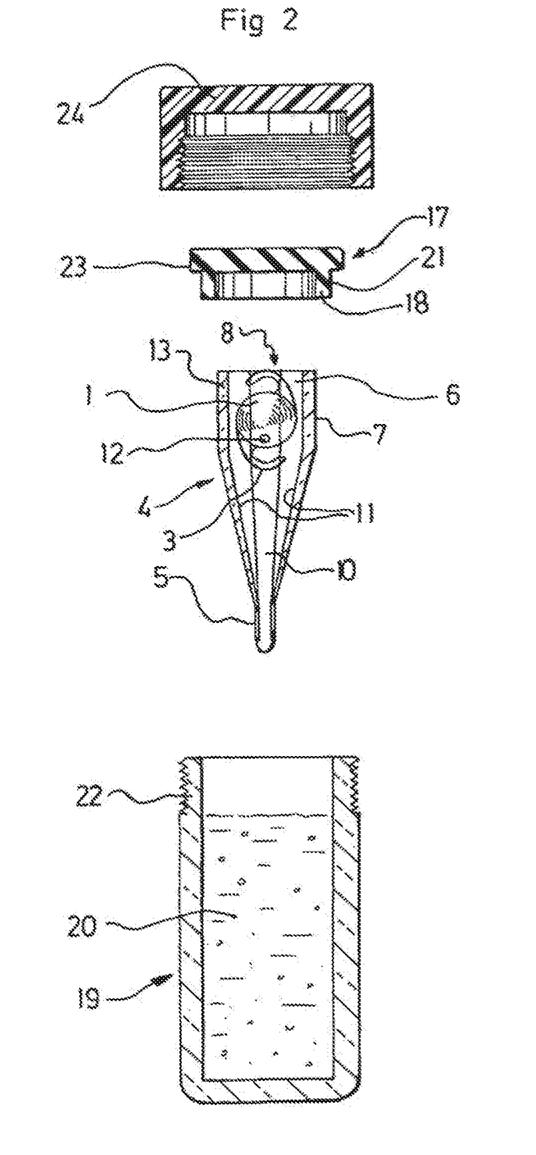
FIG. 2 is an exploded schematic view in axial section of the device of FIG. 1, the outer envelope not being shown.

In the first variant of the invention illustrated, the injection support 4 is carried by a flexible rubber stopper 17 having a cylindrical female extension 18 adapted to receive the cylindrical end 7 of the injection support 4 in such a way that the injection support 4 is then carried by the stopper 17. However, the connection of the stopper 17 to the injection support 4 is detachable in that the injection support 4 can be removed from the stopper 17 by simply moving the two parts apart.

The stopper 17 is also adapted to close in a sealed manner a rigid flask 19 containing a bath of liquid solution 20 for conserving the flexible hydrophilic lens 1, the injection support 4 and the lens 1 being immersed in the bath of liquid solution 20.

The cylindrical outer wall 21 of the extension 18 of the stopper 17 is adapted to be inserted in the neck 22 (open axial end) of the flask 19 and close it in a sealed manner. The cylindrical wall 21 is prolonged outside the neck 22 by a disc-shaped portion 23 which covers the end edge of the neck 22.

The stopper 17 of flexible rubber is preferably itself covered by a rigid closing cap 24 adapted to cover the whole stopper assembly in a sealed manner and to be screwed onto the rigid flask 19, the stopper 17 being squeezed and held in place between the neck 22 and the cap 24. The rigid cap 24 is provided with an internal screw thread adapted to cooperate with a matching thread of the outer wall of the neck 22 of the rigid flask. The rigid flask 19 is preferably made of glass or synthetic material, transparent or otherwise, adapted to withstand steam sterilization and made, in particular, of polycarbonate or polymethacrylate.

The liquid solution 20 contained in the rigid flask 19 does not entirely fill the internal volume of the rigid flask 19, even after the injection support 4 has been inserted and the rigid flask 19 has been closed. A sufficient volume of air must be retained inside the rigid flask 19 to be able to absorb pressure variations induced during subsequent steam sterilization. The sealed closure of the rigid flask 19 formed by the stopper 17 and the cap 24 is liquid-tight but not totally impermeable to gases, and in particular to pressurized gases such as water vapor.

The rigid flask 19 containing the injection support 4 with a lens 1 is itself enclosed in the interior of a flexible outer packaging envelope compatible with steam sterilization. Such flexible outer packaging envelopes are well known per se, in particular for packaging surgical instruments. It is adapted to allow water vapor to pass freely into the interior of the cavity that it delimits, but subsequently to protect its contents from any possibility of bacterial contamination, and is liquid-tight.

The assembly of the packaging device thus formed contains an unfolded flexible hydrophilic lens ready for use inside the injection support 4, and said lens 1 is bathed in the liquid conserving solution 20 in the flask 19. The whole assembly can be steam-sterilized by being placed in an autoclave at a pressure and a temperature and for a duration adapted to permit sterilization of the envelope 25, the flask 19, the injection support 4 and the lens 1.

Before placing the lens 1 in such a packaging device it is, of course, preferable to ensure that all the different elements of said packaging device are themselves sterilized. Likewise, the packaging is preferably produced in conditions which are as sterile as possible and according to the applicable standards After steam-sterilization, the envelope 25 may be provided in a manner known per se with one or more colored marking(s) guaranteeing the sterile state and known per se.

To utilize a lens 1 packaged in this way it is sufficient to open the flexible envelope 25 in order to extract the flask 19, to open the rigid cap 24, to remove the stopper 17, to separate the injection support 4 from the stopper 17 and to connect the injection support 4 to an injection device 14, itself previously sterilized. As can be seen, all the above actions can be carried out while all the elements are in a sterile state without specific handling of the lens 1, itself already in position in its injection support 4. The injection device 14 and the injection support 4 can be used immediately to implant the lens 1 through an incision formed in the patient's eye.

Figure 3:
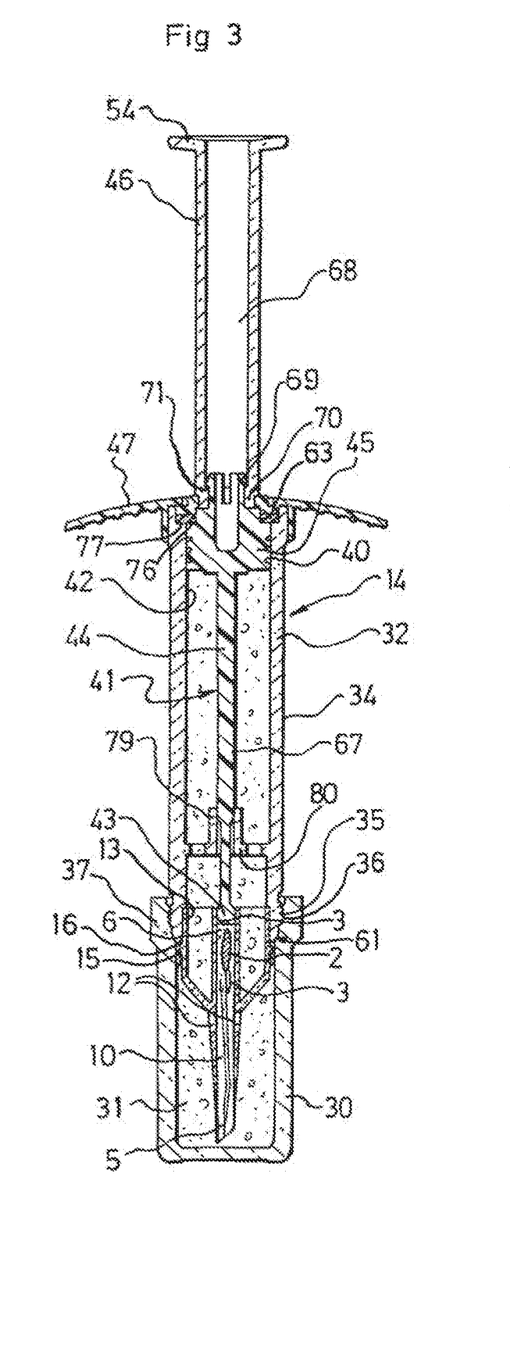
FIGS. 3 and 4 are schematic views in axial section in two different section planes of the packaging device according to a second, preferred embodiment of the invention, the outer envelope not being shown.
Figure 4:
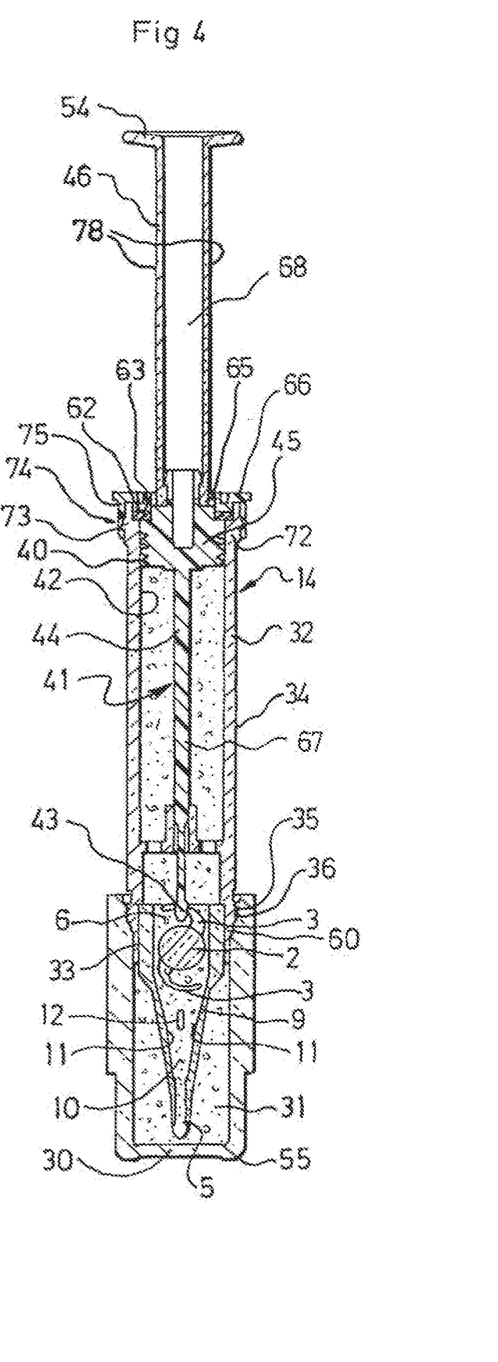

In the second preferred variant of the invention illustrated, the injection support 4 has been previously fixed to the injection device 14 which serves as the stopper for the rigid flask 30 containing the bath of liquid solution 31 for conserving the lens 1. In other words, the rigid flask 30 is used to cover and close in a liquid-tight manner the implantation end 5 of the injection support 4.

The injection device 14 comprises a hollow cylindrical body 32, one end of which forms the cylindrical axial end 33 provided with apertures 16 for receiving the fixing lugs 15 of the injection support 4. The outer cylindrical wall 34 of said end 33 has an external thread 35 adapted to cooperate with an internal thread 36 formed in the neck 37 of the flask 30. In the example shown, the flask 30 is cylindrical and its neck 37 is formed by the open axial end of said cylindrical flask, that is, it has the same diameter as the rest of the flask. The thread 35 and the thread 36 are adapted to lock when fully screwed together and tightened, producing a liquid-tight seal between them. Thus, they may have a variable self-locking pitch of the type referred to as a "gas or pipe thread". To ensure liquid-tightness between the outer cylindrical wall 34 and the flask 30, a tapered male face 60 is provided at the end of the outer wall 34 and a matching tapered female face 61 is provided in the neck 37 of the flask 30, said faces 60, 61 being adapted to come into contact with one another when the parts are fully screwed together. As a variant (not shown), a seal may be provided between the faces 60, 61 or at another location in the assembly.

The portion of the injection support 4 extending axially outside the injection device 14 after fixing extends wholly inside the volume of the rigid flask 30. To facilitate screwing and unscrewing of the flask 30, the latter is advantageously provided with projecting external ribs 38.

In this way, the rigid flask 30 can be fixed rigidly and in a sealed manner to the hollow cylindrical body 32 simply by screwing. However, it is likewise possible subsequently to unscrew the rigid flask 30 from the cylindrical body 32 so as to separate the rigid flask 30 from the injection support 4 and from the injection device 14 in order to inject the lens 1.

The hollow cylindrical body 32 incorporates a thruster piston 41 comprising an injection rod 44 extending axially inside an axial bore 42 of the cylindrical body 32. The thruster piston 41 includes an axial ejection end 43 adapted to come into contact with the lens 1 positioned in the receptacle 6 and to push said lens 1 axially through the folding cone 9, then through the implantation end 5 until the ejection end 43 itself emerges from the implantation end 5 in order to correctly implant the lens 1 in the internal cavity of the eye. However, in the packaged state the thruster piston 41 is retracted inside the hollow cylindrical body 32, without its ejection end 43 being in contact with the lens 1.

The ejection end 43 of the thruster piston 41 is formed at the end of the injection rod 44 of the thruster piston 41, the length of which is adapted to be able to be inserted completely inside the internal conduit formed in the injection support 4, that is, in the receptacle 6, the folding cone 9 and the implantation end 5. In other words, if L1 is the length of the injection rod 44 of the thruster piston and L2 is the length of the internal conduit of the injection support 4 from the opening 8 of the receptacle 6 to the implantation end 5, it must be ensured that:

$$L1 > L2 + \varepsilon,$$

where ε is a length sufficient to ensure that the second haptic of the lens 1 is ejected when the injection rod 44 is pushed fully into the injection support 4.

The ejection end 43 of the thruster piston 41 preferably has a concave or forked configuration to cooperate with the lens 1.

Opposite the ejection end 43, the injection rod 44 of the thruster piston 41 is formed integrally with a sealing block 45 adapted to close transversely and sealingly the axial bore 42 of the hollow cylindrical body 32. The sealing block 45 may be formed of flexible synthetic material in the manner of a piston of a syringe, having a plurality of lips or toric seals 40, its transverse cross-section matching that of the bore 42. The thruster piston 41 is prolonged beyond the sealing block 45 opposite the injection rod 44 by a rigid operating stem 46 which extends axially outside the hollow cylindrical body 32 and can be pushed axially into the bore 42 in order to implant the lens 1. The length of the hollow cylindrical body 32 corresponds to that of the operating stem 46 so as to permit manipulations and translational movements of the thruster piston 41 into the cylindrical body 32, in order to implant the lens as indicated above.

The end 72 of the hollow cylindrical body 32 opposite the narrowed end 33 has an operating collar 47 like that of a syringe, projecting radially to facilitate depression of the operating stem 46 of the thruster piston 41.

In the embodiment shown in the Figures, the thruster piston 41 is formed by two distinct parts assembled together axially, namely a first part 67 forming the injection rod 44 of the thruster piston 41 and the sealing block 45, and a second part 68 forming the operating stem 46. For assembling the two parts 67, 68 to one another the sealing block 45 has opposite the injection rod 44 a split snap-in plug 69 extending axially, and the end 70 of the operating stem 46 is open and provided with a shoulder 71 for locking onto the snap-in plug 69.

The hollow cylindrical body 32 is also formed by two distinct parts, namely a first, main part forming the hollow cylindrical body 32 and a second axial end piece 66 closing the hollow cylindrical body at its axial end 72 opposite its end 33 which receives the injection support 4.

When the end piece 66 is not in position, the first part 67 of the thruster piston 41 can be introduced into the bore 42 of the hollow cylindrical body 32. Once the part 67 has been introduced, the end piece 66 can be placed on the end of the cylindrical body 32 to close it. In this case, too, the end piece 66 can be fitted to the end 72 of the hollow cylindrical body 66 by simple elastic engagement and locking, for example, by means of lugs 73 in the form of latching elements projecting radially outwards from the wall 34 of the hollow cylindrical body 32, and matching openings 74 formed in a skirt 75 of the end piece 66 for receiving the lugs 73.

The end piece 66 also forms the operating collar 47.

Furthermore, the end piece 66 is adapted to form an axial end stop 62 preventing premature extraction of the thruster piston 41, i.e. extraction of the injection rod 44 and the sealing block 45, from the hollow cylindrical body 32. This axial end stop 62 is formed by a collar-shaped surface of the end piece 66 adapted to receive axially an opposed collar-shaped surface 76 of the sealing block 45. An annular seal 63 is advantageously interposed between the axial end stop 62 and the sealing block 45. This seal 63 may be trapped between the stop 62 formed by the end piece 66 and a shoulder 77 of the wall of the hollow cylindrical body 32. Thus, when the sealing block 45 is pushed axially towards the end 72 of the hollow cylindrical body under the effect of the pressure of the liquid prevailing in the interior of the bore 42 (in particular during steam-sterilization), the sealing block 45 compresses the seal 63, ensuring complete sealing and preventing any leakage of liquid.

The end piece 66 closing the hollow cylindrical body is also provided with a central axial opening 65 through which the operating stem 46 passes when it is depressed in order to inject the lens. This opening 65 advantageously has a transverse cross-section which is not rotationally symmetrical. For example, its cross-section has the overall shape of a circle cut by two diametrically opposed chords formed by opposed flat faces. The end 70 of the part 68 forming the operating stem 46 has radial dimensions smaller than the distance between the two opposed flat faces of the opening 65, so that said end 70 can rotate freely in the opening 65. By contrast, the principal running element of the part 68 forming the operating stem 46 has a transverse cross-section which is not rotationally symmetrical but has a shape and dimensions matching those of the opening 65 through which it must slide. In the example shown, the operating stem 46 therefore has two diametrically opposed flat faces 78. When the flat faces 78 are axially aligned with the opposed flat faces of the opening 65, the stem 46 can be introduced through the opening 65 and the thruster piston 41 can be depressed in order to inject the lens. Conversely, when the flat faces 78 of the operating stem 46 are not aligned with the flat faces of the opening 65, through rotation of the operating stem 46 about its longitudinal axis and around the plug 69, the operating stem 46, which is outside the hollow cylindrical body and the end piece 66, cannot be inserted into the opening 65. In this way means of locking the thruster piston 41 in its retracted end position in the hollow cylindrical body 32 are produced. However, these locking means can be unlocked simply by rotating the stem 46. The locking means prevent premature actuation of the thruster piston 41 before use, in particular when the assembly is packaged and handled for transportation.

Moreover, the injection rod 44 of the thruster piston 41, of smaller diameter than the sealing block 45, is advantageously guided inside the bore 42 in the region of the end 33 of the body 32 by a cylindrical guide 79 having a shape and dimensions matching those of the rod 44. The guide 79 is connected to the wall 34 of the hollow cylindrical body 32 by a flange 80 provided with openings allowing liquid to pass through when the piston is displaced. To prevent rotation of the rod 44 and the sealing block 45 around their axis, the transverse cross-section of the stem 44, like that of the guide 79, is advantageously not rotationally symmetrical, being, for example, square.

The injection device 14 thus formed is comparable to a syringe, the sealing block of which is prolonged by the injection rod 44.

The injection device 14 is formed in one piece from a material adapted to withstand steam sterilization, for example, from polycarbonate or polymethacrylate (PMMA).

To package a lens 1, the lens 1 is placed flat in the receptacle 6 of an injection support 4, the injection support 4 is fixed to the end of the cylindrical body 32 of the injection device 14, and the injection support 4 and the end 33 of the hollow cylindrical body 32 are introduced into the rigid flask 30 by screwing the latter onto the outer wall of the hollow cylindrical body 32 until a liquid-tight seal is obtained. Prior to this, the rigid flask 30 contains a quantity of liquid conserving solution so adapted that after the rigid flask 30 has been fitted to the hollow cylindrical body 32 the lens 1 is bathed in the liquid solution 31. It should also be noted that prior to the fitting of the rigid flask 30 a quantity of liquid solution may be introduced into the interior of the conduit of the injection support 4 and of the bore 42 of the hollow cylindrical body 32. The whole assembly is then bathed in the liquid conserving solution.

The liquid-tightness of the rigid flask 30 closed by the injection device 14 is obtained, firstly, between the hollow cylindrical body 32 and the neck 37 of the flask via the screw threads 36 and 35 and, secondly, between the sealing block 45 of the thruster piston 41 and the hollow cylindrical body 32 by means of the lips or seals 40 and the seal 63. Thus, it is the injection device 14 which itself serves as the stopper for the rigid flask 30. It might be considered, inversely, that it is the rigid flask 30 which serves as the stopper for the injection device 14.

After the rigid flask 30 and the injection device 14 have been positioned and assembled with the injection support 4 in the rigid flask 30, the whole assembly can be placed in a flexible packaging envelope 48, then steam-sterilized at a temperature and a pressure and for a duration adapted to achieve sterilization. At the end of sterilization there is no risk of the thruster piston 41 being ejected from the cylindrical body 32 through pressure differentials.

To utilize a packaging device according to this second embodiment of the invention, it is sufficient to extract the assembly formed by the injection device 14 and the rigid flask 30 from the envelope 48, to unscrew the flask 30 from the cylindrical body 32 so as to extract therefrom the injection support 4 carrying the lens 1, and then immediately to utilize the injection device carrying the injection support 4 to implant the lens 1. As can be seen, no handling of the lens 1 is necessary and the latter is perfectly conserved in a sterile state within the liquid solution contained in the rigid flask 30.

The invention may be subject to numerous variants with respect to the preferred embodiments described hereinbefore and illustrated in the Figures, which variants may also be combined. The specific forms of the different elements and the choice of materials, and the relative dimensions, may be different to those described and illustrated.

The invention provides a device which is ready for use and is completely sterile, while avoiding any handling of the lens, the latter, like the injection device 14 and the injection support 4, being maintained in a completely sterile condition.

What is claimed is:

1. A device for packaging and conserving in a sterile condition a flexible hydrophilic intraocular lens comprised therein and for intraocular implantation of the lens, comprising:
   an injection support including an implantation end through which the lens can be slid and ejected for intraocular implantation, said injection support adapted to receive and carry the lens and associated with an injection device including a thruster piston able to push the lens towards the implantation end of the injection support; and
   a flexible hydrophilic intraocular lens placed on the injection support;
   wherein the injection support is adapted to receive and carry the lens flat and to carry out folding of the lens prior to ejection of the latter via the implantation end,
   wherein the injection device includes a hollow cylindrical body for receiving the thruster piston adapted to slide in a sealed manner in the cylindrical body,
   wherein the lens is placed flat on the injection support and is immersed in a liquid conserving solution contained within a liquid-tight rigid flask and the hollow cylindrical body of the injection device, which bathes the lens and keeps the lens hydrated, the injection support extending in the liquid conserving solution in the rigid flask,
   wherein the rigid flask and the cylindrical body are adapted to be fixed rigidly and sealingly to one another, but in such a way that they can be separated from one another in order to utilize the injection device to implant the lens,
   wherein an interior surface of the rigid flask has a first mating fastener,
   wherein an exterior of the hollow cylindrical body has a second mating fastener complimentary to the first mating fastener, and
   wherein the device is in a sterilised condition.

2. The device and flexible hydrophilic intraocular lens comprised therein as claimed in claim 1, wherein the injection support is adapted to carry out the folding by a simple translational movement imparted to the lens when the latter is pushed towards the implantation end.

3. The device and flexible hydrophilic intraocular lens comprised therein as claimed in claim 1, wherein the rigid flask and the cylindrical body are fixed to one another by screwing an end of the rigid flask to the outer wall of the cylindrical body in such a way as to ensure liquid-tightness between the rigid flask and the outer wall of the cylindrical body.

4. The device and flexible hydrophilic intraocular lens comprised therein as claimed in claim 1, further comprising an axial end stop which prevents premature extraction of the thruster piston from the hollow cylindrical body.

5. The device and flexible hydrophilic intraocular lens comprised therein as claimed in claim 4, wherein the hollow cylindrical body is adapted to form the axial end stop preventing premature extraction of the thruster piston from the hollow cylindrical body.

6. The device and flexible hydrophilic intraocular lens comprised therein as claimed in claim 5, wherein it includes a seal adapted to be interposed between the axial end stop of the hollow cylindrical body and a sealing block of the thruster piston when in its retracted end position in the hollow cylindrical body.

7. The device and flexible hydrophilic intraocular lens comprised therein as claimed in claim 1, further comprising unlockable means for locking the thruster piston in its retracted end position in the hollow cylindrical body.

8. The device and flexible hydrophilic intraocular lens comprised therein as claimed in claim 7, wherein the thruster piston includes a non-rotationally-symmetrical operating stem, wherein the hollow cylindrical body has an axial end provided with a non-rotationally-symmetrical opening having a shape matching that of the operating stem, and
    wherein the operating stem is so mounted as to be able to be rotated about its longitudinal axis between a locked position in which the operating stem cannot pass through the opening and an unlocked position in which the operating stem can pass through the opening.

9. The device and flexible hydrophilic intraocular lens comprised therein as claimed in claim 1, wherein the injection support includes an adapter bush forming a receptacle for the lens, the bush being adapted to be able to carry and receive different models of lens, and to be mounted in a cylindrical end portion of the injection support.

10. The device and flexible hydrophilic intraocular lens comprised therein as claimed in claim 1 further enclosed in an outer packaging envelope compatible with steam sterilization.

11. The device and flexible hydrophilic intraocular lens comprised therein as claimed in claim 1, wherein the first mating fastener and second mating fastener are threaded fasteners.

12. The device and flexible hydrophilic intraocular lens comprised therein as claimed in claim 1, further comprising an adapter bush press fit into the injection support, the adapter bush having lateral clips for supporting the lens.

13. The device and flexible hydrophilic intraocular lens comprised therein as claimed in claim 12, further comprising an external rib on the adapter bush; and
    a groove on an inner surface of the injection support, the groove cooperating with the external rib.

\* \* \* \* \*